United States Patent
Lin et al.

(10) Patent No.: US 9,765,079 B2
(45) Date of Patent: Sep. 19, 2017

(54) CRYSTALLINE FORMS OF PEMETREXED DIACID AND MANUFACTURING PROCESSES THEREFOR

(71) Applicant: ScinoPharm Taiwan, Ltd., Tainan (TW)

(72) Inventors: Ying-Tzu Lin, Tainan (TW); Kuan-Hsun Wang, Tainan (TW); Wei-Shuo Lo, Tainan (TW); Wen-Wei Lin, Tainan (TW); Wan-Yin Cheng, Tainan (TW)

(73) Assignee: SCINTOPHARM TAIWAN, LTD., Tainan (TW)

( * ) Notice: Subject to any disclaimer, the term of this patent is extended or adjusted under 35 U.S.C. 154(b) by 0 days.

(21) Appl. No.: 15/150,720

(22) Filed: May 10, 2016

(65) Prior Publication Data

US 2017/0121334 A1 May 4, 2017

Related U.S. Application Data

(62) Division of application No. 14/924,909, filed on Oct. 28, 2015, now Pat. No. 9,604,990.

(60) Provisional application No. 62/072,540, filed on Oct. 30, 2014.

(51) Int. Cl.
*C07D 487/00* (2006.01)
*C07D 487/04* (2006.01)

(52) U.S. Cl.
CPC ................................. *C07D 487/04* (2013.01)

(58) Field of Classification Search
None
See application file for complete search history.

(56) References Cited

U.S. PATENT DOCUMENTS

| 2008/0045711 A1 | 2/2008 | Busolli et al. |
| 2011/0172424 A1 | 7/2011 | Luo et al. |
| 2011/0196155 A1 | 8/2011 | Busolli et al. |
| 2012/0329819 A1 | 12/2012 | Albrecht et al. |

FOREIGN PATENT DOCUMENTS

| WO | WO-0162760 A2 | 8/2001 |
| WO | WO-2008124485 A2 | 10/2008 |

OTHER PUBLICATIONS

Taylor, et. al., J. Med. Chem. 1992, 35, 4450-4454.*
International Search Report for Application No. PCT/SG2015/050399, dated Jan. 29, 2016.
Miwa et al., A Novel Synthetic Approach to Pyrrolo [2,3-d] pyrimidine Antifolates. J Org Chem. 1993;58:1696-1701.

* cited by examiner

*Primary Examiner* — Jeffrey H Murray
(74) *Attorney, Agent, or Firm* — Mintz, Levin, Cohn, Ferris, Glovsky and Popeo, P.C.

(57) ABSTRACT

Crystalline forms of pemetrexed diacid are provided (Forms 1 and 2) which are readily produced for either laboratory-scale or industrial scale. Processes for the preparation of Forms 1 and 2 are also provided.

16 Claims, 2 Drawing Sheets

CRYSTALLINE FORMS OF PEMETREXED DIACID AND MANUFACTURING PROCESSES THEREFOR

CROSS-REFERENCES TO RELATED APPLICATIONS

This application is a divisional application of U.S. patent application Ser. No. 14/924,909, filed Oct. 28, 2015, now U.S. Pat. No. 9,604,990 issued on Mar. 28, 2017, and claims the benefit of priority to U.S. Provisional Application No. 62/072,540, filed Oct. 30, 2014, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

It is reported that pemetrexed is chemically similar to folic acid and is in the class of chemotherapy drugs called folate antimetabolites. Pemetrexed works by inhibiting some enzymes used in purine and pyrimidine synthesis, such as thymidylate synthase (TS), dihydrofolate reductase (DHFR), and glycinamide ribonucleotide formyltransferase (GARFT). By inhibiting the formation of precursor purine and pyrimidine nucleotides, pemetrexed prevents the formation of DNA and RNA, which are required for the growth and survival of both normal cells and cancer cells. The only version of this chemotherapy drug in the market currently is pemetrexed disodium (brand name Alimta) which is manufactured and marketed by Eli Lilly and Company, and used for the treatment of pleural mesothelioma and non-small cell lung cancer. Pemetrexed diacid is a critical precursor of the preparation of pemetrexed disodium. It is believed that pemetrexed diacid also has excellent anti-tumor activities as pemetrexed disodium. So far, many crystalline forms of pemetrexed diacid have been reported in several patents/applications. For example:

1) US2008045711A1 ('711 application) filed by Sicor, Inc. discloses seven crystalline forms of pemetrexed diacid including two crystalline forms of a hydrate (crystalline forms A and B), a crystalline form of a DMSO solvate (crystalline form C), two crystalline forms of a DMF solvate (crystalline forms D and E), and two anhydrous crystalline forms (crystalline forms F and G). US2011172424A1 discloses three crystalline forms of pemetrexed diacid and these crystalline forms are defined as a crystalline form of hydrate (crystalline forms H, I and J). Each of these crystalline forms has their inevitable shortcoming. For example, solvents incorporated in crystalline forms C, D and E have higher boiling points and can be difficult to remove, resulting in the increased burden of controlling the solvent residues during the preparation of a drug product. For the anhydrous crystalline forms F and G, a very high temperature (160-200° C.) is needed in the drying step, which may result in a greater risk of pemetrexed diacid degradation. The hydrate crystalline forms A and B also have their deficiencies during preparation. For example, the crystalline form A is difficult to filter which can result in a time-consuming operation and low yield. As to the crystalline form B, its crystallization period is very long and lacks efficiency. Specifically, up to about 18 hours are needed for the crystallization step alone.

2) US2011172424A1 ('424 application) filed by Chongqing Pharmaceutical Research Institute Co., Ltd. discloses three crystalline forms of hydrate (crystalline forms H, I and J). Among these crystalline forms, the yield of the crystalline form H is only about 60%. Further, the specification of the '424 application describes the method for preparing crystalline form H, wherein "pemetrexed diacid is directly dissolved in a mixed solvent consisting of water and water-miscible solvent." The dissolution may be promoted by adjusting pH value or heating, wherein pH value is usually adjusted to pH 1-3 and heating is usually from 40° C. to near boiling point of the mixed solution. These conditions can be disadvantageous as heating a mixed solution at a high temperature for dissolution can result in development of unwanted discoloration that may require additional steps for color treatment. Crystalline form I, suffers from low yield. According to Example 5 ('424 application), if the water content of pemetrexed disodium (wet product) is assumed an optimized percentage (e.g., 10%), then the yield of pemetrexed diacid is only about 42.5%. As to the crystalline form J, Example 6 of the '424 application discloses that the mixture of pemetrexed disodium and water needs to be cooled to 0-5° C. After a pH adjustment, the reaction mixture was further stirred only for a short period of time (e.g., about 10 min). Regarding these operation conditions, one of ordinary skill in the art should be aware that the purpose of cooling the mixture of pemetrexed disodium and water to a low temperature and stirring the reaction mixture for a short period of time after a pH adjustment is to prevent a crystalline form from transferring to another known crystalline form, such as the crystalline forms A or B as disclosed in the '711 application. However, these procedures are not conducted under mild condition and may increase the operational difficulty of pemetrexed diacid preparation on a large scale.

Given the above, there remains a need in the art to develop other new crystalline forms of pemetrexed diacid in order to overcome the shortcomings of crystalline forms of pemetrexed diacid. Surprisingly, two novel crystalline forms of pemetrexed diacid have been identified that are stable and prepared easily on a large scale, and have good crystallinity.

BRIEF SUMMARY OF THE INVENTION

Pemetrexed, N-[4-[2-(2-amino-4,7-dihydro-4-oxo-1H-pyrrolo[2,3-d]pyrimidin-5-yl)ethyl]benzoyl]-L-glutamic acid, also known as pemetrexed diacid, has the following formula:

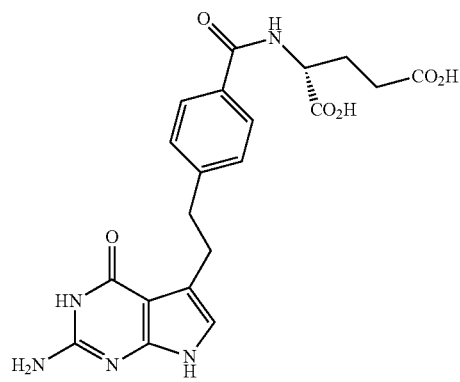

Pemetrexed diacid

The present application relates to novel crystalline forms of pemetrexed diacid and manufacturing processes therefor. These novel crystalline forms are useful for the development of a pharmaceutical composition containing pemetrexed acid.

In accordance with the first aspect of the present invention, a novel crystalline form of pemetrexed diacid (hereafter designated as crystalline Form 1) is provided, and is characterized by a powder X-ray diffraction ("PXRD") pattern with peaks at about 13.3, 15.8, 21.2, 26.2 and 26.7±0.2 degrees two-theta.

Preferably, the crystalline Form 1 is further characterized by a powder X-ray diffraction pattern with peaks at about 7.7, 14.4, 16.6, 17.0 and 18.7±0.2 degrees two-theta. More preferably, the crystalline Form 1 is further characterized by a powder X-ray diffraction pattern with peaks at about 11.5, 16.1, 17.5, 20.0 and 24.4±0.2 degrees two-theta.

The crystalline Form 1 is preferably characterized by a powder X-ray diffraction pattern as substantially depicted in FIG. 1.

The crystalline Form 1 may be further characterized by data selected from a group consisting of: a weight loss of about 9.7% to about 10.3% at a temperature up to 120° C., as measured by thermal gravimetric analysis ("TGA"). Typically, the crystalline Form 1 provided in the present application is a hydrated form and preferably has a weight loss of about 8% to about 11% at a temperature up to 120° C., as measured by thermal gravimetric analysis ("TGA").

In accordance with the second aspect of the present invention, a novel crystalline pemetrexed diacid (hereafter designated as crystalline Form 2) is provided, and is characterized by a powder X-ray diffraction ("PXRD") pattern with peaks at about 9.0, 12.7, 14.4, 16.3 and 25.3±0.2 degrees two-theta.

Preferably, the crystalline Form 2 is further characterized by a powder X-ray diffraction pattern with peaks at about 13.4, 13.8, 17.2, 25.9 and 27.3±0.2 degrees two-theta.

More preferably, the crystalline Form 2 is further characterized by a powder X-ray diffraction pattern with peaks at about 15.5, 18.1, 18.4, 27.9 and 31.6±0.2 degrees two-theta.

The crystalline Form 2 is preferably characterized by a powder X-ray diffraction pattern as substantially depicted in FIG. 2.

The crystalline Form 2 may be further characterized by data selected from a group consisting of: a weight loss of about 0.6% to about 1.3% at a temperature up to 120° C., as measured by thermal gravimetric analysis ("TGA"). Typically, the crystalline Form 2 of pemetrexed diacid provided in the present application is an anhydrous form and preferably has a weight loss of about not more than 1.5% at a temperature up to 120° C., as measured by thermal gravimetric analysis ("TGA").

In accordance with the third aspect of the present invention, a process for preparing the crystalline Forms 1 and 2 of pemetrexed diacid is provided.

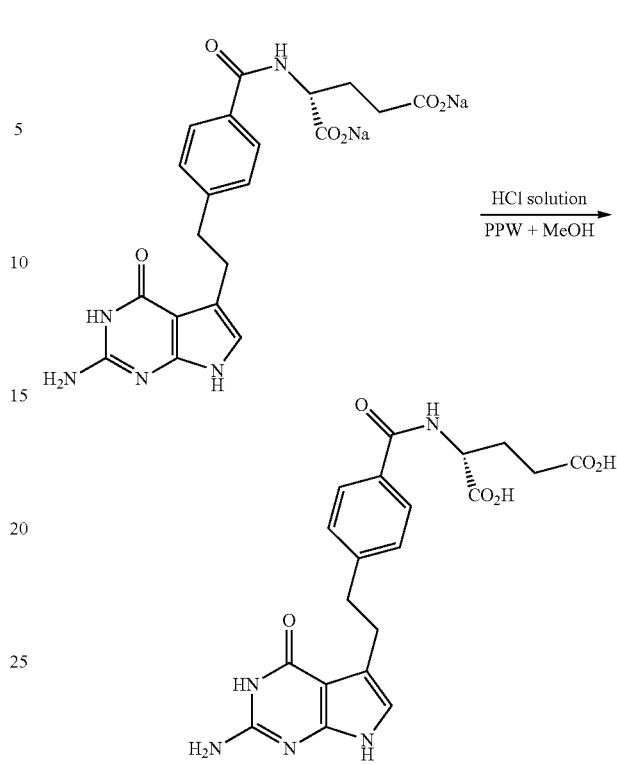

The process for preparing the crystalline Form 1 of pemetrexed diacid comprises:
a) dissolving pemetrexed disodium in a mixture of methanol and water to form a solution;
b) adjusting the pH value of the solution to about 2.5 to 3.5 with an acid;
c) isolating the precipitate; and
d) drying the precipitate at room temperature to obtain the crystalline Form 1 of pemetrexed diacid.

The process for preparing the crystalline Form 2 of pemetrexed diacid comprises:
a) dissolving pemetrexed disodium in a mixture of water and methanol to form a solution;
b) adjusting the pH value of the solution to about 2.5 to 3.5 with an acid;
c) isolating the precipitate; and
d) drying the precipitate at about 60-90° C. to obtain the crystalline Form 2 of pemetrexed diacid.

DETAILED DESCRIPTION OF THE INVENTION

General

Two novel crystalline forms of pemetrexed diacid have been identified that are stable and have good crystallinity. Moreover, in the preparation process, no other crystalline forms were identified (either from a direct formation or inter-conversion of one form to another), even after stirring the reaction mixtures for several hours or overnight; or adjusting the pH of the mixture. The processes described herein are advantageous as they are conducted under mild reaction conditions and very easy to practice. More importantly, these processes can provide a high yield (>90%) of the novel crystalline forms of pemetrexed diacid and are suitable for the manufacture of pemetrexed diacid on a large scale.

Embodiments of the Invention

The present application provides novel crystalline forms of pemetrexed diacid and manufacturing processes therefor. These novel crystalline forms are useful for the development of a pharmaceutical composition containing pemetrexed acid. According to the processes described herein, the crystalline forms can be prepared which are substantially free of the earlier described crystalline forms. The term "substantially free" refers to an amount of 10% or less of another form, preferably 8%, 5%, 4%, 3%, 2%, 1%, 0.5%, or less of another form.

The present application comprises a crystalline pemetrexed diacid (hereafter designated as Form 1) characterized by a powder X-ray diffraction ("PXRD") pattern with peaks at about 13.3, 15.8, 21.2, 26.2 and 26.7±0.2 degrees two-theta.

In one embodiment, the present application comprises the crystalline Form 1 further characterized by a powder X-ray diffraction pattern with peaks at about 7.7, 14.4, 16.6, 17.0 and 18.7±0.2 degrees two-theta.

In another embodiment, the present application comprises the crystalline Form 1 preferably characterized by a powder X-ray diffraction pattern with peaks at about 11.5, 16.1, 17.5, 20.0 and 24.4±0.2 degrees two-theta.

Figure 1:
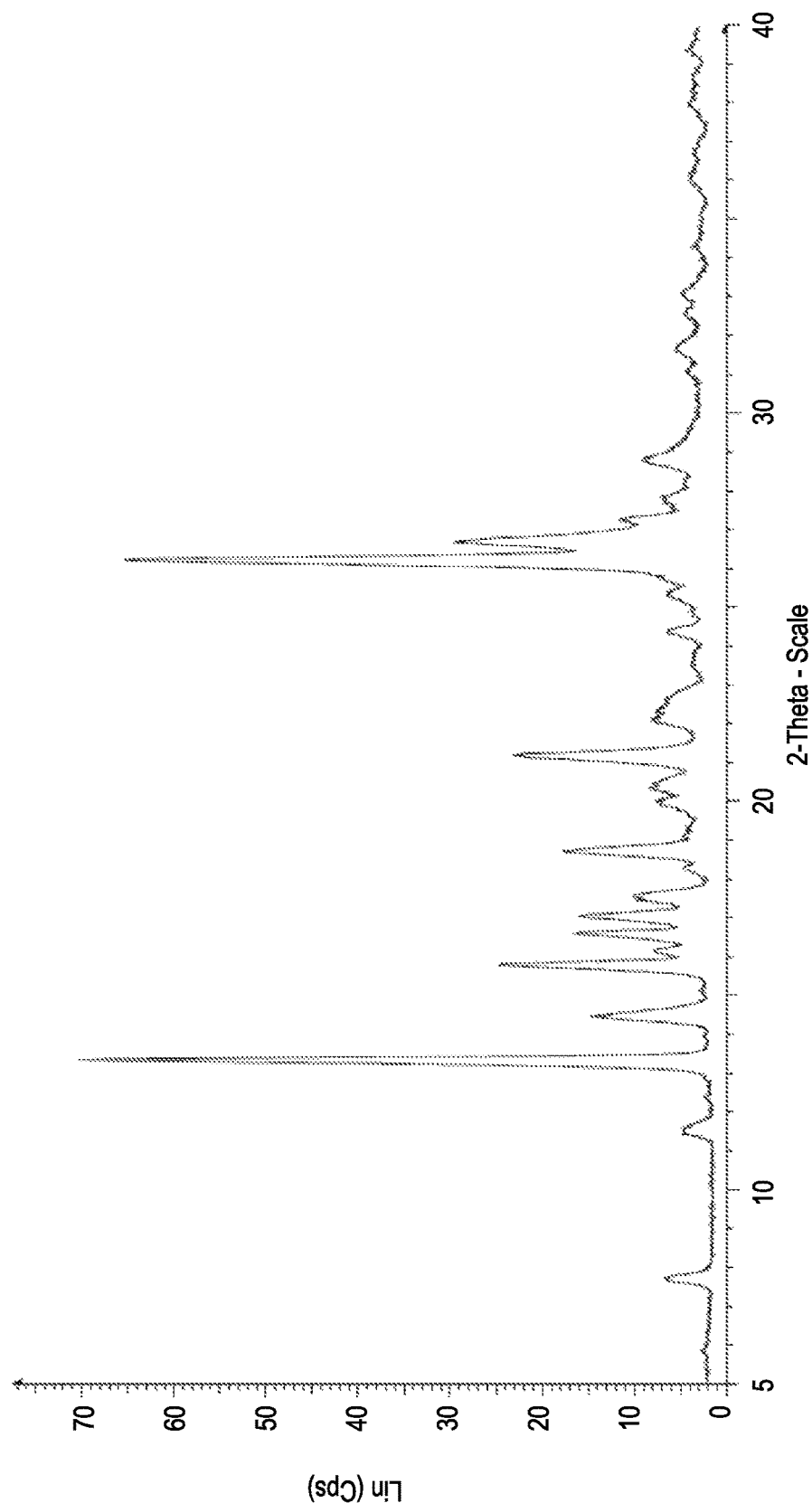
FIG. 1 illustrates a powder X-ray diffraction pattern of crystalline pemetrexed diacid characterized by a powder X-ray diffraction pattern with peaks at about 13.3, 15.8, 21.2, 26.2 and 26.7±0.2 degrees two-theta.

In another embodiment, the present application comprises the crystalline Form 1 more preferably characterized by a powder X-ray diffraction pattern as substantially depicted in FIG. 1.

In yet another embodiment, the crystalline pemetrexed diacid Form 1 may be further characterized by a weight loss of about 8% to about 11% at a temperature up to 120° C., as measured by thermal gravimetric analysis ("TGA").

In still another embodiment, the crystalline pemetrexed diacid Form 1 may be further characterized by data selected from a group consisting of: a weight loss of about 9.7% to about 10.3% at a temperature up to 120° C., as measured by thermal gravimetric analysis ("TGA"), and a powder X-ray diffraction pattern with peaks at about 13.3, 15.8, 21.2, 26.2 and 26.7±0.2 degrees two-theta.

Typically, the crystalline form 1 of pemetrexed diacid is a hydrated form.

The present application also comprises a crystalline pemetrexed diacid (hereafter designated as Form 2) characterized by a powder X-ray diffraction ("PXRD") pattern with peaks at about 9.0, 12.7, 14.4, 16.3 and 25.3±0.2 degrees two-theta.

In one embodiment, the present application comprises the crystalline Form 2 further characterized by a powder X-ray diffraction pattern with peaks at about 13.4, 13.8, 17.2, 25.9 and 27.3±0.2 degrees two-theta.

In another embodiment, the present application comprises the crystalline Form 2 preferably characterized by a powder X-ray diffraction pattern with peaks at about 15.5, 18.1, 18.4, 27.9 and 31.6±0.2 degrees two-theta.

Figure 2:
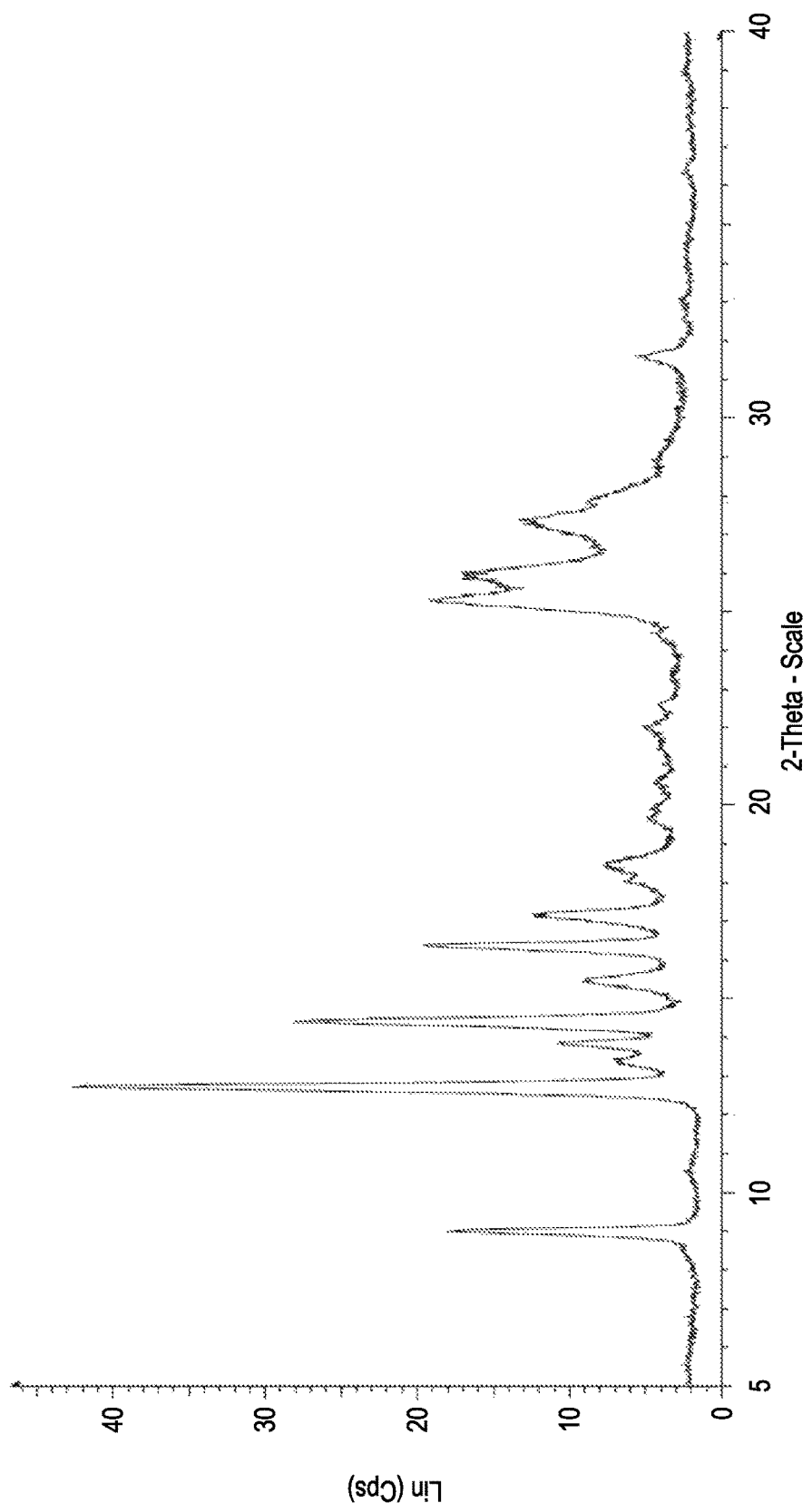
FIG. 2 illustrates a powder X-ray diffraction pattern of crystalline pemetrexed diacid characterized by a powder X-ray diffraction pattern with peaks at about 9.0, 12.7, 14.4, 16.3 and 25.3±0.2 degrees two-theta.

In another embodiment, the present application comprises the crystalline Form 2 more preferably characterized by a powder X-ray diffraction pattern as substantially depicted in FIG. 2.

In yet another embodiment, the crystalline pemetrexed diacid Form 2 may be further characterized by a weight loss of about 1.5% or less at a temperature up to 120° C., as measured by thermal gravimetric analysis ("TGA").

In still another embodiment, the crystalline pemetrexed diacid Form 2 is may be further characterized by data selected from a group consisting of: a weight loss of about 0.6% to about 1.3% at a temperature up to 120° C., as measured by thermal gravimetric analysis ("TGA"), and a powder X-ray diffraction pattern with peaks at about 9.0, 12.7, 14.4, 16.3 and 25.3±0.2 degrees two-theta.

Typically, the crystalline form 2 of pemetrexed diacid is an anhydrous form.

The present application also provides a process for preparing the crystalline Form 1 of pemetrexed diacid. The process comprises crystallizing pemetrexed diacid by the following steps of a)-d):

a) dissolving pemetrexed disodium in a mixture of water and methanol to form a solution;
b) adjusting the pH value of the solution to about 2.5 to 3.5 with an acid;
c) isolating the precipitate; and
d) drying the precipitate at room temperature to obtain the crystalline Form 1 of pemetrexed diacid.

Typically, the process for preparing the crystalline Form 1 of pemetrexed diacid comprises: dissolving pemetrexed disodium in the mixture of water and methanol having a solvent ratio of 3:1 to 1:1 (v/v).

Preferably, the process for preparing the crystalline Form 1 of pemetrexed diacid comprises: dissolving pemetrexed disodium in the mixture of water and methanol at a temperature of about 15-30° C. to form a solution.

More preferably, the process for preparing the crystalline Form 1 of pemetrexed diacid comprises: adjusting the pH value of the solution to about 3 to obtain a suspension comprising a precipitate of the crystalline Form 1 of pemetrexed diacid.

Typically, the pH of the solution is adjusted to about 3 by adding an inorganic acid or an organic acid. Preferably, the acid is added by a form of dilute aqueous solution. Preferably, the acid is an inorganic acid selected from a group consisting of: hydrochloric acid (HCl), hydrobromic acid (HBr), hydroiodic acid (HI), sulfuric acid ($H_2SO_4$), and mixtures thereof; or an organic acid selected from a group consisting of: acetic acid, trifluoroacetic acid, methanesulfonic acid, toluenesulfonic acid, and mixtures thereof. More preferably, the acid is hydrochloric acid or acetic acid.

Typically, the addition of the acid induces precipitation of the crystalline pemetrexed diacid. Typically, the precipitate of pemetrexed diacid is isolated from the suspension by filtration.

The process may further comprise: washing the precipitate of pemetrexed diacid with a solvent. Preferably, the solvent is water or a mixture of water and a water miscible solvent.

More preferably, the solvent is water or a mixture of water and a water miscible solvent which is adjusted to a pH value of about 3. Most preferably, the solvent is a mixture of water and methanol which is adjusted to a pH value of about 3.

In one group of embodiments, the precipitate of pemetrexed diacid is dried with nitrogen purging at room temperature. Preferably, the precipitate of pemetrexed diacid is dried with nitrogen purging at a temperature of about 15-30°

C., more preferably about 25° C. Preferably, the time period on drying the precipitate of pemetrexed diacid is for about at least 1 to 8 hours, and more preferably for at least 2 to 6 hours, although longer periods of drying are also suitable.

The present application further provides a process for preparing the crystalline Form 2 of pemetrexed diacid.

The process comprises crystallizing pemetrexed diacid by the following steps of a)-d):
a) dissolving pemetrexed disodium in a mixture of methanol and water to form a solution;
b) adjusting the pH value of the solution to about 2.5 to 3.5 with an acid;
c) isolating the precipitate; and
d) drying the precipitate at a temperature of 60-90° C. to obtain the crystalline Form 2 of pemetrexed diacid.

Typically, the process for preparing the crystalline Form 2 of pemetrexed diacid comprises: dissolving pemetrexed disodium in the mixture of water and methanol having a solvent ratio of 3:1 to 1:1 (v/v).

Preferably, the process for preparing the crystalline Form 2 of pemetrexed diacid comprises: dissolving pemetrexed disodium in the mixture of water and methanol at a temperature of about 15-30° C. to form a solution.

More preferably, the process for preparing the crystalline Form 2 of pemetrexed diacid comprises: adjusting the pH value of the solution to about 3 to obtain a suspension comprising a precipitate of the crystalline Form 2 of pemetrexed diacid.

Typically, the pH of the solution is adjusted to about 3 by adding an inorganic acid or an organic acid. Preferably, the acid is added by a form of dilute aqueous solution. Preferably, the acid is an inorganic acid selected from a group consisting of: hydrochloric acid (HCl), hydrobromic acid (HBr), hydroiodic acid (HI), sulfuric acid ($H_2SO_4$), and mixtures thereof; or an organic acid selected from a group consisting of: acetic acid, trifluoroacetic acid, methanesulfonic acid, toluenesulfonic acid, and mixtures thereof. More preferably, the acid is hydrochloric acid or acetic acid.

Typically, the addition of the acid induces precipitation of the crystalline pemetrexed diacid. Typically, the precipitate of pemetrexed diacid is isolated from the suspension by filtration.

The process may further comprise: the precipitate of pemetrexed diacid may be washed with a solvent. Preferably, the solvent is water or a mixture of water and a water miscible solvent. More preferably, the solvent is water or a mixture of water and a water miscible solvent which is adjusted to a pH value of about 3. Most preferably, the solvent is a mixture of water and methanol which is adjusted to a pH value of about 3.

Typically, the precipitate of pemetrexed diacid is dried with nitrogen purging at an appropriate temperature for a time period. Preferably, the precipitate of pemetrexed diacid is dried with nitrogen purging at a temperature of 60-90° C., more preferably about 70° C. Preferably, the time period on drying the precipitate of pemetrexed diacid is for about 4 hours to about 22 hours, and more preferably for about 12 hours.

EXAMPLES

Experimental Methodology

X-ray Powder Diffraction patterns were collected on a Bruker AXS D8 diffractometer using Cu Kα1 radiation (40 kV, 40 mA), θ-2θ goniometer, and divergence of V4 and receiving slits, a Ge monochromator and LynxEye detector. The representative XRPD pattern was collected under ambient condition. The details of the scanning parameters are:
Angular range: 5-40°
Step size: 0.02°
Scan speed: 0.6 sec/step Thermal Gravimetric Analysis TGA and DSC data was collected on a Mettler Toledo instrument TGA/DSC 1. Each sample (5-15 mg) was loaded onto a pre-tared alumina crucible and the balance and furnace were purged with nitrogen prior to the analysis with a flow rate set as 40±5 and 60±5 mL/min, respectively. The heating process was programmed to start from 30° C. and stop at 350° C. with a 10° C./min ramp.

Examples described herein comprise a process for preparing crystalline forms of pemetrexed diacid suitable for either laboratory-scale or industrial scale. The present application includes, but is not limited to the following examples.

Example 1

Preparation of the Crystalline Form 1 of Pemetrexed Diacid 10 g of pemetrexed disodium was added to 200 mL of water and 100 mL of methanol at about 22° C. The resulting mixture was stirred until complete dissolution was achieved. The pH value of the resulting solution was about 8.1. About 15 mL of 1N hydrochloric acid aqueous solution was added and the pH value was adjusted to 5.6, followed by stirring for about 13 hours. About 24.1 mL of 1N hydrochloric acid aqueous solution was added and the pH value was adjusted to 2.9, followed by stirring for about 2 hours. The resulting suspension was filtered and the solid was washed with 40 mL of water to obtain a wet cake. The wet cake was dried by nitrogen purging for at least 2 hours to provide the crystalline Form 1 of pemetrexed diacid. The PXRD pattern of the dried pemetrexed diacid was measured and illustrated in FIG. 1.

Example 2

Preparation of the Crystalline Form 2 of Pemetrexed Diacid

The crystalline Form 1 provided in Example 1 was placed in an oven and dried at 40° C. under vacuum (150 torr) for about 15.5 hours and at 80° C. for another 5 hours. The crystalline Form 2 of pemetrexed diacid was provided.

Example 3

Preparation of the Crystalline Forms 1 and 2 of Pemetrexed Diacid 10 g of pemetrexed disodium was added to 200 mL of water and 100 mL of methanol at about 22° C. The resulting mixture was stirred till complete dissolution. The pH value of the resulting solution was about 8. About 15 mL of 1N hydrochloric acid solution was added and the pH value was adjusted to 5.7, followed by stirring for about 1 hour. About 25 mL of 1N hydrochloric acid solution was added and the pH value was adjusted to 2.9, followed by stirring for about 2 hours. The resulting suspension was filtered and the solid was washed with 40 mL of water to obtain a wet cake. The wet cake was purged with nitrogen, and then dried at 40° C. under vacuum (150 torr) for about 15.5 hours to provide about 8.45 g pemetrexed diacid, followed by drying at 60 to 90° C. to provide the crystalline Form 2 of pemetrexed diacid (97.9% yield).

Example 4

Preparation of the Crystalline Form 2 of Pemetrexed Diacid 10 g of pemetrexed disodium was added to 200 mL of water and 100 mL of methanol at about 25° C. The resulting mixture was stirred till complete dissolution. The pH value of the resulting solution was about 8.1. About 20 mL of 1N acetic acid solution was added and the pH value was adjusted to 5.5, followed by stirring for about 1 hour. About 50 mL of 1N acetic acid solution was added and the pH value was adjusted to 5.2, followed by stirring overnight. About 40 mL of 3N acetic acid solution was added and the pH was adjusted to 4.5, 40 mL of 9N acetic acid solution was added and the pH value was adjusted to 3.9, and then 60 mL of glacial acetic acid was added and the pH value was adjusted to 3.3 at about 20° C. The resulting suspension was filtered and the solid was washed with 40 mL of water to obtain a wet cake. The wet cake was purged with nitrogen, and then dried under vacuum at 40° C. for about 17 hours and at 80° C. for about 5 hour to provide the crystalline Form 2 of pemetrexed diacid.

Example 5

Preparation of the Crystalline Form 2 of Pemetrexed Diacid 10 g of pemetrexed disodium was added to 200 mL of PPW and 100 mL of methanol at about 22° C. The resulting mixture was stirred till complete dissolution and the pH value of the resulting solution was about 8.4. About 15 mL of 1N hydrochloric acid solution was added and the pH value was adjusted to 5.5, followed by stirring for about 1 hour. About 25 mL of 1N hydrochloric acid solution was added and the pH value was adjusted to 2.9, followed by stirring for about 2 hour. The resulting suspension was filtered and the solid was washed with 100 mL of water/methanol (v/v=2/1) to obtain a wet cake. The wet cake was purged with nitrogen, and then dried at 70° C. under vacuum (150 torr) for about 15.5 hours to provide about 8.06 g of the crystalline Form 2 of pemetrexed diacid having a weight loss of about 0.6% (98.5% yield).

Example 6

Preparation of the Crystalline Form 2 of Pemetrexed Diacid 10.07 g of pemetrexed disodium was added to 200 mL of water and 100 mL of methanol at about 15° C. The resulting mixture was stirred till complete dissolution and the pH value of the resulting solution was about 8.4. 12.2 mL of 1N HCl was added and the pH value was adjusted to 5.6, followed by stirring for about 1 hour. 26.1 mL of 1N HCl was added and the pH value was adjusted to about 2.8, followed by stirring for 1 hour. The resulting suspension was filtered and the solid was washed with about 60 mL of water/methanol (v/v=2/1) to obtain a wet cake. The wet cake was purged with nitrogen, and then dried at 80° C. under vacuum (100 torr) for at least 4 hours to provide the crystalline Form 2 of pemetrexed diacid as white solid.

Example 7

Preparation of the Crystalline Form 2 of Pemetrexed Diacid 10 g of pemetrexed disodium was added to 200 mL of water and 100 mL of methanol at about 30° C. The resulting mixture was stirred till complete dissolution and the pH value of the resulting solution was about 7.9. 15.4 mL of 1N HCl was added and the pH value was adjusted to 5.5, followed by stirring for about 1 hour. 23.1 mL of 1N HCl was added, and the pH value is adjusted to about 3, followed by stirring for 1 hour. The resulting suspension was filtered and the solid was washed with about 100 mL of water/methanol (v/v=2/1) to obtain a wet cake. The wet cake was purged with nitrogen, and then dried at 70° C. under vacuum (100 torr) for 9 hours to provide about 8.25 g of the crystalline Form 2 of pemetrexed diacid (NLT 90% yield).

Example 8

Preparation of the Crystalline Form 2 of Pemetrexed Diacid for Large Scale 150 g of pemetrexed disodium was added to 3000 g of water and 1500 g of methanol at 15 to 25° C. (target 20° C.). 225 mL of 1N HCl was added at 15 to 25° C. (target 20° C.) and the pH value was adjusted to about 5.6 where the cloud point is reached. The mixture was stirred at cloud point for 1 hour, and then 375 mL of 1N HCl was added at 15 to 25° C. and the pH value was adjusted to about 2.5 to 3.5 (target 3.0). The resulting mixture was stirred at 15 to 25° C. (target 20° C.) for 2 hours, and then filtered. The filtered solid was washed with 600 mL of HCl aqueous solution (pH=2.6) to obtain a wet cake. The wet cake was purged with nitrogen for at least 2 hours, and then dried at 70° C. under vacuum (100 to 120 torr) for at least 12 hours to provide 103 g of the crystalline Form 2 of pemetrexed diacid having a weight loss of about 0.8% (NLT 87% yield) as white solid (purity is 99.76%). The PXRD pattern of the dried pemetrexed diacid was measured and illustrated in FIG. 2.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A crystalline Form 1 of pemetrexed diacid, characterized by a powder X-ray diffraction pattern with peaks at about 13.3, 15.8, 21.2, 26.2 and 26.7±0.2 degrees two-theta, wherein the crystalline Form 1 is substantially free of other crystalline forms of pemetrexed diacid.

2. The crystalline Form 1 of pemetrexed diacid of claim 1, further characterized by a powder X-ray diffraction pattern with peaks at about 7.7, 14.4, 16.6, 17.0 and 18.7±0.2 degrees two-theta.

3. The crystalline Form 1 of pemetrexed diacid of claim 2, further characterized by a powder X-ray diffraction pattern with peaks at about 11.5, 16.1, 17.5, 20.0 and 24.4±0.2 degrees two-theta.

4. The crystalline Form 1 of pemetrexed diacid of claim 1, characterized by a powder X-ray diffraction pattern as substantially depicted in FIG. 1.

5. The crystalline Form 1 of pemetrexed diacid of claim 1, further characterized by a weight loss of about 8% to about 11% at a temperature up to 120° C., as measured by thermal gravimetric analysis.

6. The crystalline Form 1 of pemetrexed diacid of claim 1, wherein the crystalline Form 1 of pemetrexed diacid is a hydrated form.

7. The crystalline Form 1 of pemetrexed diacid of claim 1, which is substantially free of other crystalline forms of pemetrexed diacid.

8. The crystalline Form 1 of pemetrexed diacid of claim 1, wherein the crystalline Form 1 of pemetrexed diacid contains 10% or less of another form.

9. The crystalline Form 1 of pemetrexed diacid of claim 1, wherein the crystalline Form 1 of pemetrexed diacid contains 5% or less of another form.

10. The crystalline Form 1 of pemetrexed diacid of claim 1, wherein the crystalline Form 1 of pemetrexed diacid contains 3% or less of another form.

11. The crystalline Form 1 of pemetrexed diacid of claim 1, wherein the crystalline Form 1 of pemetrexed diacid contains 1% or less of another form.

12. A process for preparing the crystalline Form 1 of pemetrexed diacid of claim 1, wherein the process comprises:
   a) dissolving pemetrexed disodium in a mixture of water and methanol at a temperature of about 15-30° C. to form a solution;
   b) adjusting the pH of the solution to a range of 2.5 to 3.5 with an acid to form a precipitate;
   c) isolating the precipitate; and
   d) drying the precipitate at a temperature of 15-30° C. to provide the crystalline Form 1 of pemetrexed diacid.

13. The process of claim 12, wherein the mixture of water and methanol has a volume ratio of 3:1 to 1:1 (water:methanol).

14. The process of claim 12, wherein the acid is an inorganic acid selected from the group consisting of: HCl, HBr, $H_2SO_4$, and mixtures thereof.

15. The process of claim 12, wherein the acid is an organic acid selected from the group consisting of: acetic acid, trifluoroacetic acid, methanesulfonic acid, toluenesulfonic acid, and mixtures thereof.

16. The process of claim 12, wherein the crystalline Form 1 of pemetrexed diacid is isolated substantially free of other crystalline forms of pemetrexed diacid.

* * * * *